United States Patent [19]

Drury

[11] 4,199,866
[45] Apr. 29, 1980

[54] DENTAL AMALGAMATION APPARATUS

[75] Inventor: Frederick H. Drury, Winterburn, Canada

[73] Assignee: Weatherford Oil Tool Co., Ltd., Edmonton, Canada

[21] Appl. No.: 808,416

[22] Filed: Jun. 20, 1977

[30] Foreign Application Priority Data

Mar. 18, 1977 [CA] Canada .................................. 274242

[51] Int. Cl.² .................................................. A61C 3/00
[52] U.S. Cl. ...................................... 366/139; 366/602
[58] Field of Search ...... 32/40 A; 98/115 R, 115 LH, 98/115 VM; 23/292; 55/385 R; 51/273; 366/602, 139, 60; 34/55

[56] References Cited

U.S. PATENT DOCUMENTS

| | | | |
|---|---|---|---|
| 2,799,935 | 7/1957 | Hall | 32/40 A |
| 3,347,530 | 10/1967 | Platt | 366/602 |
| 3,808,750 | 5/1974 | Mann | 51/273 |
| 3,890,720 | 6/1975 | Nichols | 34/55 |
| 3,956,458 | 5/1976 | Anderson | 55/6 |
| 4,059,903 | 11/1977 | Piet et al. | 32/40 R |
| 4,108,509 | 8/1978 | Piet et al. | 32/40 A |

FOREIGN PATENT DOCUMENTS

| | | | |
|---|---|---|---|
| 207273 | 4/1908 | Fed. Rep. of Germany | 32/40 A |
| 642305 | 2/1937 | Fed. Rep. of Germany | 32/40 A |

Primary Examiner—Louis G. Mancene
Assistant Examiner—John J. Wilson
Attorney, Agent, or Firm—Beveridge, DeGrandi, Kline & Lunsford

[57] ABSTRACT

The invention provides a dental amalgamator which prevents mercury vapor, given off during amalgamation, from polluting the air in the neighborhood of the amalgamator. The amalgamator comprises a casing carrying a capsule holder and a drive means for the holder, a lid movable to a closed position in which it cooperates with the casing to form an enclosure for a capsule held by the holder, the enclosure having air inlets allowing air to flow from the atmosphere into the enclosure. A vacuum pump is arranged to communicate with the enclosure via a mercury filter medium, so that during amalgamation air is drawn into the enclosure, over the capsule, and then through the mercury filter where mercury vapors are removed.

11 Claims, 3 Drawing Figures

DENTAL AMALGAMATION APPARATUS

BACKGROUND OF THE INVENTION

The present invention relates to dental amalgamators of the type which rapidly vibrate a capsule containing an amalgam mixture, so as to thoroughly mix the ingredients. The object of the invention is to provide an amalgamator in which the mercury vapors given off during amalgamation are largely prevented from entering the air in the neighbourhood of the amalgamator.

The high speed mixing of dental amalgams which is achieved in present day amalgamators, along with the attendant rises in temperature, produce mercury vapors which usually enter the air around an amalgamator, and which can cause quite high levels of mercury in this air. In fact, tests in the vicinity of present day amalgamators show that there is frequently a concentration of mercury three or more times higher than the normally acceptable limits for health.

It has been proposed to remove the mercury vapor from the air in places such as dentists surgeries by use of an extraction fan and filter, such arrangement being shown in U.S. Pat. No. 3,956,458 which issued May 11, 1976 to Anderson. Such an arrangement however does not prevent an operator from breathing in mercury vapors when he or she is near to the amalgamator.

Also, efforts have been made to produce a completely leak-proof capsule which does not give off any vapor during amaglamation. However, the fact that such a capsule is leak-proof ensures that a pressure of mercury vapor is built up in the capsule during the amalgamation due to heat generated during mixing, so that a substantial amount of the mercury vapor is still released when the capsule is opened.

The present invention provides an amalgamator in which the amount of mercury vapor which can enter the air surrounding the amalgamator is very substantially reduced.

In accordance with one aspect of the invention, a dental amalgamator comprises a casing carrying a capsule holder and drive means therefor, a lid movable from an open position allowing access to the capsule holder to a closed position in which it cooperates with the casing to form an enclosure for a capsule held by the holder, and in which the enclosure has air inlet means allowing air to flow from the atmosphere into the enclosure. The enclosure communicates with an outlet adapted for connection to a vacuum source, whereby during amalgamation air may be drawn by the vacuum source into the enclosure, the air being mixed with mercury vapors within the enclosure and then being drawn through the outlet into the vacuum source. With this arrangement, the air which flows into the enclosure during amalgamation, being drawn by the vacuum source, purges the mercury vapor from the enclosure during amalgamation. Preferably, the flow of air is continued sometime after amalgamation has ceased, for most effective removal of mercury vapors.

The amalgamator described above may be attached to a remote source of vacuum, such as an exhaust fan. However, in the preferred embodiment of the invention, self contained apparatus is provided which comprises a casing carrying a capsule holder and drive means therefor, a lid movable from an open position allowing access to the capsule holder to a closed position in which it cooperates with the casing to form an enclosure for a capsule held by the holder, the enclosure having air inlet means allowing air to flow from the atmosphere into the enclosure, and the apparatus further comprises a vacuum pump arranged to communicate with the enclosure via a mercury filter medium.

BRIEF DESCRIPTION OF THE DRAWINGS

A preferred embodiment of the present invention will now be described by way of example with reference to the accompanying drawings, in which.

DESCRIPTION OF A PREFERRED EMBODIMENT OF THE INVENTION

The drawings show a self-contained type of apparatus including the amalgamator 10 itself, and a stand 12 which contains a vacuum pump and mercury vapor filter, as well as some electrical controls for the amalgamator.

Figure 2:
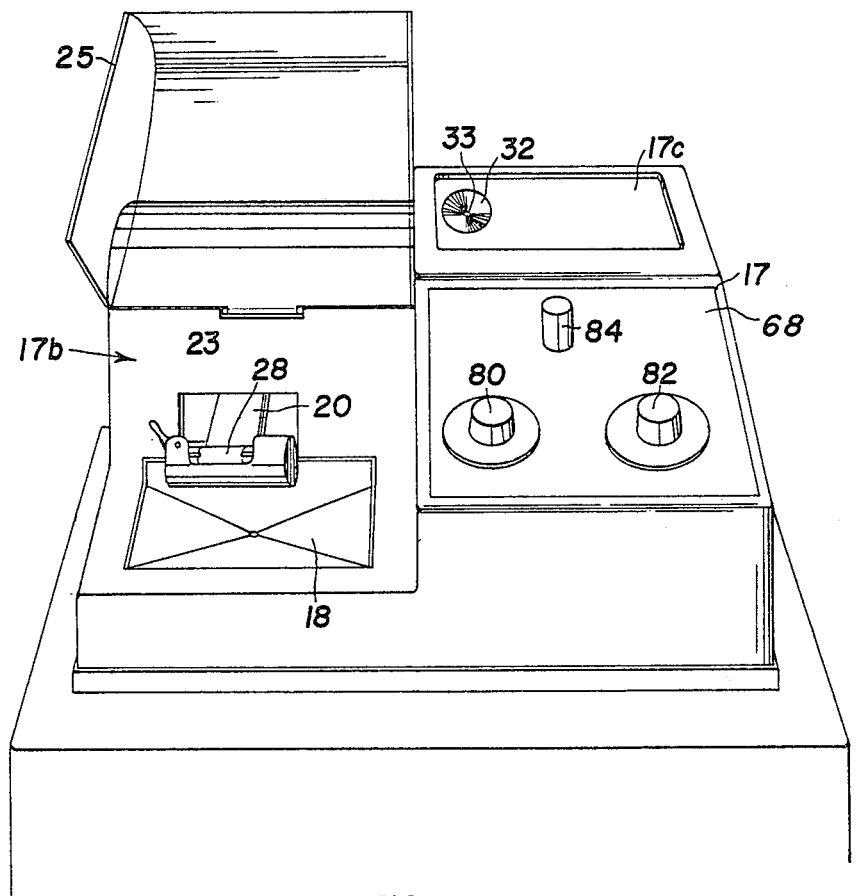
FIG. 2 shows enlarged views of the top portion of the amalgamator.

The amalgamator 10 has a casing comprising a base plate 15 and housing parts 17 and 18 attached to the base plate by screws, these parts being of molded plastic. The main housing part is a hollow molding 17 the cross-sectional shape of the main part of which is shown at 17a in FIG. 3. Ths molding 17 however has a recessed front portion 17b occupying a left hand side part of the molding as shown in FIG. 2, and also as shown in FIG. 2 the right hand side of the molding has a raised rear platform portion 17c. The recessed portion 17b has a rectangular cutout area at the base thereof, the outline of which is shown in FIG. 2, and which receives a separate molded tray part 18 supported by pillars 18a directly from the base plate, so that the molding 17 can be removed from the base plate while leaving tray part 18 in place. Above and to the rear of the tray part 18 the recessed part 17b of the main body molding is provided with an aperture 20 for the amalgamator arm.

At the top center of the recessed portion 17b is a further small recess 23, the ends of which provide sockets for hinge means 24 used to mount a curved lid 25. This lid has a top and front portion having the shape indicated in FIG. 3, and also has a side portion arranged substantially to close the left hand side of the recess 17b, so that when the lid is closed as in FIG. 3 it forms an enclosure with the recess 17b and the tray 18 and which surrounds a capsule 28 held by a capsule holder described below. The lower edge of the lid when closed is spaced slightly from the front of molding 17, so that air inlet means is provided between the lid and the molding 17 for a purpose to be described. The lid can be moved to the open position shown in FIG. 2 allowing free access to the recessed portion 17b, and is of transparent plastics to allow the capsule to be seen when the lid is closed.

The tray 18, forming the base of the amalgamation enclosure, has a concave upper surface with a central drainhole 29 at its lowest point. This drainhole 29 is directly above an outlet port 15a in the base plate 15, so that any mercury spilled within the enclosure can pass from drainhole 29 and down through outlet 15a.

Figure 1:
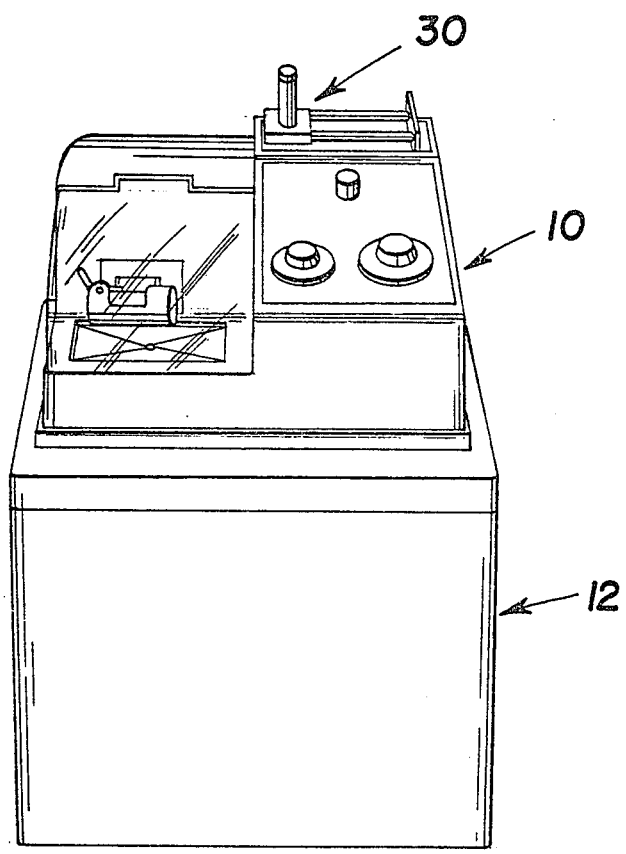
FIG. 1 shows a perspective view of a self-contained amalgamator and vacuum filter apparatus.

The raised rear platform portion 17c of the casing has a rectangular recessed area intended to provide a resting place for a measuring and dispensing apparatus for the amalgam mixture. This apparatus is shown at 30 in FIG. 1, and is a standard item which is described in detail in Canadian Pat. No. 842,637, issued May 26, 1970 to General Refineries Inc. The dispensing apparatus 30 has means for receiving silver alloy pellets, and mercury, and for dispensing correct quantities of these into a capsule 28 before this is loaded into the amalgamator. Dispensing apparatus of this kind frequently drips small amounts of mercury, and for this purpose the platform portion 17c is provided with a recessed area 32 at the left hand side, having a drainhole 33 at its center leading to an internal nipple in the casing to which is connected a plastic drain tube 35, shown in FIG. 3. This drain tube 35 slopes downwardly and has its outer end close to or within the outlet 15a, so that any mercury spilled from the dispensing apparatus also goes to this outlet.

The casing just described is substantially sealed except for the aperture 20, and the drainholes 29 and 33 referred to, and the outlet 15a.

Also all exterior surfaces of the casing are smooth and rounded for easy cleaning and removal of any spilled mercury.

A rear portion of the base plate 15 carries a spring mounting plate 40 which carries at its right hand end an electric motor 41. The left hand end of the motor has a spindle 42 which is angled and eccentric to the rotary axis of the motor, and which is rotatable within a sleeve portion 44a of a capsule holder arm 44.. Arm 44 projects fowardly from the motor through the aperture 20 of the casing and into the enclosure under the lid 25. The capsule holder arm is limited against rotation on the spindle by means of upper and lower springs 46, the lower spring being connected to the plate 40 and the upper spring being connected to a support rod 47 having its lower end carried by plate 40. The forward end of the arm 44 has a capsule holder 44b which is identical to that described in our U.S. Pat. No. 4,074,900. This capsule holder holds the capsule 28 in a firm manner while vibrating the capsule within the enclosure under lid 25, the eccentric and angled nature of the spindle 42 causing the capsule to move with a figure 8 movement as is already known in the amalgamator art. As described in our the aforesaid U.S. Pat. No. 4,074,900, the capsule holder 44b is specially designed to hold the capsule very firmly while allowing this to be easily inserted and removed.

Figure 3:
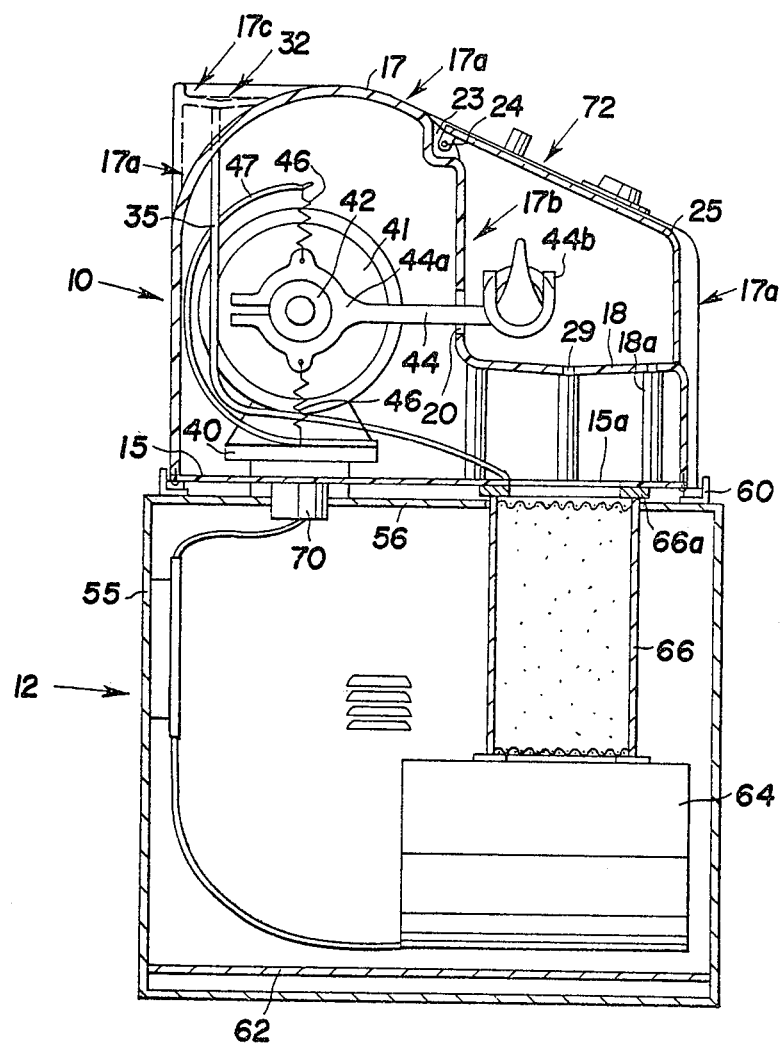
FIG. 3 shows a sectional side elevation of the apparatus shown in FIG. 1.

The amalgamator unit 10 is supported as shown best in FIG. 3 on a stand 12 which is rectangular and formed of sheet metal side panels 55 and top panel 56 and having a recess formed by angle members 60 which are located at the base of the amalgamator. Close to the bottom of the stand unit 12 is a horizontal base plate 62 which carries a combined electric motor and vacuum pump unit 64 of the kind used in vacuum cleaners. This unit is mounted so as to have its inlet at the top center. Above this unit 64 there is provided a cylindrical canister 66, the lower end of which is sealed by a gasket to the top of the unit 64, and the upper end of which passes through a locating aperture in the top panel 56 of unit 12 and is sealed by a top gasket 66a around the outlet 15a of the amalgamator casing. The canister 66 contains, between wire mesh ends, a mercury vapor filter medium which is activated carbon impregnated with sulfur, and which is the subject of U.S. Pat. No. 3,194,629 issued July 13, 1965 to Pittsburgh Activated Carbon Company. A canister of this filter medium of about 4¾ inches in length, and about 3¼ inches in diameter, is found to be suitable for use with the amalgamator, given normal usage in a dentist's surgery, for about one year before this needs changing.

The stand 12 also contains electrical controls for the motor and vacuum pump unit, these being contained on a control panel 68. From this control panel, wires lead downwardly to the vacuum pump motor, and upwardly to a socket 70 which co-operates with a four pin plug on the bottom of the amalgamator unit. This four pin plug has connections to the motor 41, and also to a control panel 72 on the right hand upper surface of the casing molding 17. As illustrated in FIG 2. this control panel has three controls, namely a knob 80 which controls the speed of amalgamation, a knob 82 which can be used to automatically control the time of amalgamation, and which includes a central start button, and an upper "mull" button 84 which causes the amalgamator motor to operate while pressed. So far as the control of the amalgamator motor is concerned, the circuits are conventional, but the control panel 68 includes additional items which cause the vacuum motor/pump unit 64 to be operated automatically when the amalgamator motor 41 is running, and to continue operation for a preselected time period after the amalgamator motor is stopped.

In addition, a switch is provided operated by the lid 25 and which prevents operation of the amalgamator motor whenever the lid is raised.

In operation, suitable alloy constitutents are placed within the capsule 28 by means of the dispensing device 30, while the capsule is held by hand. After the capsule has been closed, this is placed within the capsule holder 44b, and the lid 25 is shut. The knob 80 is set for the desired amalgamation speed, and knob 82 is set for the desired time of amalgamation. Amalgamation is commenced by pressing the button in the center of knob 82. The amalgamator motor and the vacuum pump motor are then caused to run simultaneously. During amalgamation, the vacuum pump draws air in through the air inlets provided around the lower edge of lid 25, this air passing over the capsule 28, and then out of the capsule enclosure into the casing via aperture 20. This action effectively purges the enclosure of mercury vapor released from the capsule. The mercury vapor and air is then drawn through the outlet 15a of the base plate, through the filter medium in capsule 66, this filter medium effectively removing most of all of the mercury vapor. The filtered air passes out of unit 12 through louvers in side panels 55. When amalgamation is finished, the pump remains operating, and is still operating when the lid 25 is opened, so that the pump is also effective to draw off mercury vapor given off when the capsule 28 is opened assuming that this is done, as preferred, in the vicinity of the enclosure. Any mercury which is split passes through drainhole 29 and also into the filter medium.

The filter canister 66 can easily be replaced by simply lifting the amalgamator off the stand 12, and lifting the canister 66 through the aperture at the top of the stand.

It will be evident from the above that the amalgamator unit can be used with other vacuum apparatus intended to draw off mercury vapor and air through the outlet 15a, for example a central vacuum system could be used for a number of amalgamators.

I claim:

1. A dental amalgamator comprising:
   a casing,
   a capsule holder and drive means therefor, said capsule holder being located outside the casing, said drive means being mounted within the casing, an arm connecting the capsule holder to the drive means, a lid movable to a closed position in which the lid forms with a portion of the external surface of the casing an enclosure which surrounds the capsule holder, said enclosure-forming portion of the external surface of the casing including an aperture, said enclosure having air inlet means to allow air to flow thereinto from the atmosphere, said casing being substantially sealed except for an outlet adapted for connection to a vacuum source, whereby during amalgamation air may be drawn by the vacuum source into the enclosure, the air mixing with mercury vapors within the enclosure and then being drawn through said aperture into the casing and thence out of said outlet.

2. An amalgamator according to claim 1 wherein said lid when closed engages said casing in a loose fitting manner to provide for said air inlet means around the lid.

3. An amalgamator according to claim 1, wherein said air inlet means and said aperture are disposed at opposite sides of said enclosure with the capsule holder therebetween, whereby air drawn in through the inlet means flows around a capsule held by the capsule holder before passing out through said aperture.

4. An amalgamator according to claim 1, wherein said enclosure has a concave base with a drain hole for spilled mercury at its lowest point, said drain hole communicating with said outlet.

5. An amalgamator according to claim 4, wherein said drain hole is located directly above said outlet when the amalgamator is in its normal position.

6. An amalgamator according to claim 1, wherein said casing has a recessed area suitable for receiving a mercury dispenser, said recessed area having a drainage hole through which any drops of mercury from said dispenser may pass, said drainage hole communicating with the outlet from the casing.

7. Dental amalgamator apparatus comprising an amalgamator according to claim 1, and further comprising a vacuum pump and a filter medium for mercury vapor disposed between said vacuum pump and said aperture.

8. Apparatus according to claim 7, wherein said casing communicates with said enclosure and has an outlet in the bottom thereof, and wherein said vacuum pump is located in a stand arranged to support said casing, the outlet of the casing being adapted to seal against the top inlet end of a mercury vapor filter held by said stand and having its outlet end connected with said vacuum pump.

9. Apparatus as claimed in claim 8, said casing provided with control means for controlling said amalgamator and said vacuum pump accessible when said lid is moved to its closed position.

10. Apparatus as claimed in claim 9, said control means automatically operating said vacuum pump whenever said amalgamator is operated.

11. Apparatus as claimed in claim 10, provided with switch means between said lid and said casing, said switch means preventing the operation of said amalgamator when said lid is in its open position.

* * * * *